United States Patent [19]

Osther et al.

[11] Patent Number: 5,093,230

[45] Date of Patent: * Mar. 3, 1992

[54] METHOD FOR RAPID AND SENSITIVE DETECTION OF IGM RETROVIRAL ANTIBODIES

[75] Inventors: Kurt B. Osther, Dallas; Louis M. Dyll, Rockwall, both of Tex.

[73] Assignee: Verigen, Inc., Framingham, Mass.

[*] Notice: The portion of the term of this patent subsequent to Dec. 5, 2006 has been disclaimed.

[21] Appl. No.: 365,109

[22] PCT Filed: Jul. 5, 1988

[86] PCT No.: PCT/US88/02257

§ 371 Date: May 5, 1989

§ 102(e) Date: May 5, 1989

[87] PCT Pub. No.: WO89/00609

PCT Pub. Date: Jan. 26, 1989

[30] Foreign Application Priority Data

Jul. 13, 1987 [DK] Denmark .............................. 3620/87
Jul. 13, 1987 [DK] Denmark .............................. 3722/87

[51] Int. Cl.⁵ .......................... C12Q 1/00; C12Q 1/70; G01N 33/53

[52] U.S. Cl. .......................................... 435/5; 435/7.9; 435/28; 435/239; 435/805; 435/810; 435/974; 436/501; 436/506; 436/513; 436/514; 436/516; 436/530; 436/811; 422/61; 422/70

[58] Field of Search ................ 435/7, 5, 240, 6, 172.3, 435/974, 9, 28, 239, 805, 810, 7.9; 252/92; 422/37, 61, 70; 564/150; 424/88, 89, 61, 86; 210/782; 436/511, 501, 506, 573, 574, 576, 530.81

[56] References Cited

U.S. PATENT DOCUMENTS 4,808,521  2/1989  Allen ...................................... 435/7
4,816,387  3/1989  Osther .................................... 435/5
4,885,235  12/1989  Osther et al. ......................... 435/5
4,918,000  4/1990  Schubert ................................. 435/7

OTHER PUBLICATIONS

Lin et al., (Aug. 86) Sequential Detection of Different Antigens Indured by Epstein-Barr Virus and Herpes Simplex Virus in the Same Western Blot by Using Dual Antibody Probes, J.V. vol. 59:522-4.

Primary Examiner—Robert A. Wax
Assistant Examiner—David R. Preston
Attorney, Agent, or Firm—Bryan, Cave, McPheeters & McRoberts

[57] ABSTRACT

A rapid and sensitive assay method for the detection of IgM antibody or the simultaneous detection of IgG and IgM antibody to retroviruses, including HIV-1 and HIV-2, and diagnostic test kits for carrying out the method is provided. According to the method of the invention, results are obtainable within 70 minutes.

39 Claims, No Drawings

METHOD FOR RAPID AND SENSITIVE DETECTION OF IGM RETROVIRAL ANTIBODIES

TECHNICAL FIELD

The present invention relates to a rapid and sensitive assay method for the detection of IgM antibody to retroviral antigens and the simultaneous detection of IgM and IgG antibodies to retroviral antigens. The present invention also relates to test kits for carrying out the assay method.

BACKGROUND OF THE INVENTION

Assay systems capable of detecting the presence or absence of antibodies generated in response to the presence of viral antigens are well known. Such assay systems have proved useful in, inter alia, the diagnosis of various disease and infectious states, for example, acquired immune deficiency syndrome (AIDS), AIDS related complexes (ARC or pre-AIDS), T-lymphocytic leukemia, and T-lymphocytic lymphoma.

The known assay systems, which employ antibody-antigen binding, ordinarily are designed to detect solely the presence or absence of IgG (immunoglobulin G). The appearance of detectable IgG directed to antigens in an infected/immunized individual, in many instances, does not occur until 30-40 days after initial infection. Typically, the IgG class antibodies are often present for months or years after infection or immunization with a foreign agent, such as a virus.

The presence of circulating IgG directed to an immunizing antigen during the course of infection or immunization is preceded by the presence of circulating IgM (immunoglobulin M) antibody directed against the antigen/immunogen. IgM antibody is often present as early as 14 days, possibly earlier, after infection/immunization. Unlike IgG antibody which remains for months or years after infection, IgM antibody loses titer 30-35 days after initial infection.

It is widely recognized that diagnostics which can detect antibodies other than IgG are desirable. For example, it is known that generally after confrontation with a foreign agent, the human immune system responds by generating antibodies against the foreign agent or antigen. It is believed, as previously discussed, that IgM, not IgG, is produced first. IgM is, however, a relatively short-lived antibody. While it may be produced shortly after infection, IgM specific antibodies fall, eventually below detectable levels, as IgG is produced in increasing amounts. Because IgM has a short life span, IgM specific antibodies are typically below detectable levels before many diseases can even be diagnosed using known diagnostic assay methods.

As can be appreciated, assays capable of detecting IgM will be useful in facilitating early detection of various infections and diseases. Early diagnosis facilitates treatment, and minimizes the risk of spreading infection.

The present invention overcomes the limitations associated with conventional assay techniques because it provides a Quick Western Blot assay for detecting the presence or absence of IgM class antibody alone or simultaneously with the detection of IgG.

Infections caused by the human retroviruses result in the appearance of antibodies in the serum, and other body fluids of the infected victim.

AIDS, which was first diagnosed in 1981, is known to be caused by a human retrovirus called HIV-1 (Human Immunodeficiency Virus-1). It has recently been reported that another human retrovirus, designated HIV-2 also causes AIDS.

The human retroviruses which are associated with AIDS are believed to be transmitted through intimate sexual contact as well as through blood.

Recently, investigators have become interested in two other human retroviruses, designated HTLV-I and HTLV-II. (HTLV means Human T-lymphotropic virus). Thus far, neither HTLV-I nor HTLV-II has been identified as the specific causative agent for any particular disease. These retroviruses, however, have been isolated from patients diagnosed with T-lymphocytic leukemia and lymphoma. Antibodies to HTLV-I have been also found in patients diagnosed with chronic, progressive spastic paraparesis (PSP) secondary to myelopathy. Neurology Alert, Vol. 6, no. 11, July 1988. It is presently believed that HTLV-I and HTLV-II are transmitted through blood. As more information about these retroviruses is revealed, it is predicted that as with HIV-1, all blood supplies will be screened for the presence of antibodies to HIV-2, HTLV-I and HTLV-II. Thus, as previously mentioned, it is advantageous to be able to detect the presence of IgM antibodies as well as IgG antibodies to facilitate early detection of infections and minimize the risk of spreading such infection.

DISCLOSURE OF THE INVENTION

The present invention provides a rapid and sensitive test system for detecting the presence of IgM antibody alone or simultaneously with IgG antibody against human retroviruses, including HIV-1, HIV-2, HTLV-I, HTLV-II and Equine Infectious Anemia Virus. The assay system of the invention is a modified Quick Western Blot technique which comprises incubating electrophoretically resolved viral protein with a test sample, preferably in the presence of nonfat milk proteins or polyethyleneglycol (PEG) 8000.

It has been found that milk proteins and PEG act to both enhance and accelerate specific protein binding. Consequently, test results are obtained in 70 minutes.

Like conventional Western Blot assays (such as those described by V. C. Tsang, J. Peralta, and R. Simmons, In: Methods in Enzymology, Vol. 92, Chapter 9, 1983, Academic Press, Inc.), the present method applies blotting techniques but, according to the present method, about 20-40% more viral lysate is loaded onto each electrophoresis gel. In particular, from about 60-130 ug of viral lysate is loaded onto each 10×16 cm gel rather than the 50-100 ug of viral protein used in conventional Western Blotting. However, it should be understood that the amount of viral lysate may be varied depending on the particular virus, for example, for HIV-1, HIV-2 and HTLV-II it is presently preferred to load the gels with from 60-120 ug of viral lysate, and most preferably 70-80 ug. For HTLV-I it is presently preferred to use 60-130 ug of viral proteins and most preferably 80-100 ug. Concentrations of test sample are also increased from 2-10 times over those used in the standard Western Blot, preferably 5 times. In other words, in carrying out a standard Western Blot, test samples are typically diluted 1:100, whereas in the present method it is preferred to dilute the test sample from about 1:10-1:50 and most preferably 1:20. The increase in lysate and sample concentrations facilitates a drastic reduction in incubation times and thus, results are obtained in under 70 minutes.

It is known that the amount of protein subjected to electrophoresis in the Western Blot assay is inversely related to the distinctiveness of the resulting bands, the potential for "noise bands" increasing with the amount of protein. Noise bands often appear adjacent to critical protein bands and may be mistaken therefor, making evaluation of test results difficult and increasing chances of false positives. It has, accordingly, previously been assumed that the use of relatively low antigen lysate concentrations, i.e., from about 5-10 ug of protein/$8\times10$ cm gel (50-100 ug of protein/$10\times16$ cm gel), are necessary to facilitate accurate detection of antibodies to viruses. It has now been found (see U.S. Pat. No. 4,816,387) that both antigen and sample concentrations can be increased as previously described and the assay time drastically decreased as compared with the time required for conventional Western Blot.

In one preferred embodiment of the present invention, a diagnostic test kit is provided which among other obvious advantages, such as time reduction, permits on site testing for antibodies, such as those against the AIDS virus. The diagnostic kit of the invention preferably includes predeveloped strong and weak positive and negative reference strips for evaluating the test results by visual comparison with test strips. However, to reduce costs, photographs of such strips may be substituted. Accordingly, reading the results of the test is facilitated. On site testing is particularly important in an organ transplant situation because testing can be performed on a 24 hour basis at virtually any location, and test results can be obtained within 70 minutes, comfortably within the life span of ischemic organs.

DETAILED DESCRIPTION OF THE INVENTION

Resolution of the Viral Antigen

In accordance with the method of the invention, antigen concentrate is electrophoretically resolved. HIV-1, HIV-2 and HTLV-I may be obtained from Protatek International, St. Paul, Minn. The antigen concentrate is diluted in buffer to a protein concentration at least 20%-40% greater than the 50-100 ug protein/$10\times16$ cm gel utilized in conventional Western Blot. Preferably, as previously mentioned, the antigen concentrate is diluted in buffer to a protein concentration of about 60 to 120 ug per $10\times16$ cm gel for HIV-1, HIV-2, and HTLV-II. Concentrations of 60 to 130 ug per $10\times16$ cm gel are preferred for HTLV-I. The preferred dilution buffers are 0.05M TRIS-HCl/50% glycerol, pH 8, 2.5% SDS (sodium dodecyl sulfate) and 5% mercaptoethanol or TRITON X100 in PBS buffer. Other buffers known to those skilled in the art are also suitable, such as 9M urea in 0.01M TRIS-HCl.

As noted above, the protein concentration of the antigen lysate used with the method of the invention is approximately 20 to as much as 40% higher than the 50-100 ug/$10\times16$ cm gel typically used for conventional Western Blot. See pages 380 to 381 of the guidelines published by V. C. Tsang, J. Peralta, and R. Simons, in Methods Of Enzymology, Vol. 92, Chapter 29, 1983, Academic Press Inc., which sets forth the 5-10 ug/$8\times10$ cm gel and 50-100 ug/$10\times16$ cm gel workable ranges of protein concentrations used in the conventional Western Blot assay. Before resolution, the antigen is generally first inactivated by means of known psoralen/UV irradiation techniques, and solubilized by treatment with from 0.1 to 1.0% TRITON X100 in PBS buffer. However, other inactivation and solubilization methods as are known to those skilled in the art may also be used. Then, the antigen is subjected to conventional gel electrophoresis of the type reported by Tsang et al, Methods in Enzymology, Vol. 92 (1983).

A tracking dye is preferably added to the diluted antigen to produce visible protein banding. The preferred dye is bromophenol blue. The dye is preferably prepared by dissolving 50 mg of bromophenol blue in 8 ml of glycerol, plus 1 ml each of 0.5M TRIS-HCl at pH 8.0 and $H_2O$. Other dyes, known to those skilled in the art, may also be used.

Suitable gels for the electrophoresis are also prepared in accordance with the method of Tsang et al., Methods in Enzymology, Vol. 92 (1983). A 10% resolving polyacrylamide gel with a 3% stacking gel (SDS-PAGE) is preferred because it resolves a molecular weight range of 12,000-180,000 daltons, the molecular weight range embracing the proteins of HIV-1, HTLV-I and HIV-2. However, the percentage of polyacrylamide gel may vary from 8-11% depending upon the particular virus being resolved.

In accordance with a preferred embodiment of the present invention, the resolved antigen protein and test sample (including controls) are incubated in the presence of milk proteins, preferably defatted proteins. (It is believed that the presence of fat interferes with the test.) Suitable defatted milk proteins include Carnation ® lowfat milk powder, but any defatted milk proteins as may be known are also useful. Such milk proteins are known to constitute about 60 to 90% casein, a phosphoprotein rich in serine; and from 10 to 40% of various other proteins including lactoalbumin, lactoglobulin, membrane globulin and a small amount of alkaline phosphatase, peroxidase catalase and xanthine dehydrogenase. The milk proteins may be-introduced into the assay system in one of several ways.

According to the first embodiment of the invention, the nitrocellulose paper blotted with the resolved viral antigen protein is coated with the milk proteins from a solution of buffer (e.g., PBS-Tween 20), containing about 5 to 10% milk proteins for about 60 minutes. The paper is then washed in a buffer solution not containing milk proteins (e.g., PBS-Tween 20) at room temperature for 1-5 minutes. The treated paper is then stored under humid conditions until use.

According to a second embodiment of the invention, the milk proteins are thoroughly mixed with and dissolved in the buffer solutions containing the test sample and controls. The controls and serum samples are then incubated with the nitrocellulose strips for 15 to 20 minutes. The liquid of each tube is discarded and the strips are washed with a PBS-Tween buffer at pH 7.3-7.4. The washing cycle consists of four 1 minute washings.

According to a third embodiment of the invention, the milk proteins are precoated on the nitrocellulose strips and additionally mixed with and dissolved in the buffer solution.

In accordance with another preferred embodiment, the resolved antigen protein and test sample (including controls) are incubated in the presence of polyethyleneglycol (PEG). Preferably, PEG is added to the sample dilution buffer in a concentration of from about 3 to 10% w/v and preferably 5% w/v. It should be understood that both milk proteins and PEG can be used together to enhance antigen-antibody binding.

The nitrocellulose sheets are then cut into strips approximately 2-2.5mm in width. Each strip, after appropriate labelling, is placed in a separate test tube for determination of antibodies to HIV-I viral lysate by the enzyme linked immunoassay of the invention. The nitrocellulose strips can also be placed in incubation trays for in-house testing. It should be understood, however, that an uncut sheet can be placed in an incubation tray equipped with a pressing cover rather than cut into individual strips. This technique may be well suited to in-house as opposed to on-site testing. As can be appreciated, however, on-site testing is facilitated by use of individual tubes. Also, placing the strips in individual tubes minimizes the need for handling during the assay procedure and thus, possible smearing of the fragile protein patterns with fingerprints. Using strips is also more economical than uncut sheets because less reagent is necessary to carry out the test.

Test samples, strong and weak positive and negative references are added to the tubes containing the nitrocellulose strips blotted with resolved antigen. Test samples include, but are not limited to serum, semen and other body fluids. The positive reference is typically a sample known to contain antibodies to the particular viral lysate. Positive references have been obtained from the Centers for Disease Control (CDC), Atlanta, Georgia. Positive controls for HIV-2 and HTLV-I have been obtained from Genetic Systems, Seattle, Washington. Alternatively, a positive reference may be made from any sample which has been standardized with a positive reference obtained from the CDC. Standardization typically means that the same test results were obtained in about 20 repeated runs. The positive reference is diluted 1/20 (1 part positive reference to 20 parts buffer) in PBS (phosphate buffered solution)-tween pH (7.2-7.4), preferably containing 5% nonfat milk proteins. Typically, 150 ul of the positive reference is mixed with 3 ml PBS-Tween.

The negative control is a sample known to be devoid of antibodies to the viral lysate, and is prepared by diluting 1/20 with PBS-Tween, pH 7.2-7.4. Typically, 150 ul of a negative reference is mixed with 3 ml PBS-Tween. Negative references for HIV-1 have been obtained from the CDC. Negative references for HIV-2 and HTLV-I have been obtained from Genetic Systems, Seattle, Washington.

As the assay method of the invention is a qualitative rather than quantitative determination, the positive and negative references are used to evaluate the test results by comparison with the results obtained from test samples.

A reagent control may also be included as a quality control feature of the present invention and is used to assure accurate functioning of the test. Normally, the reagent control is the buffer used to dilute test samples and controls. Preferably, PBS-Tween, pH 7.2-7.4 is used as the reagent control. However, the reagent control is not necessary during routine readings of the strips.

As indicated hereinabove, when employing the milk protein treatment and/or PEG of the present invention, test samples may be used which are more concentrated than those used in conventional Western Blot to accelerate the binding of antibody against the antigen contained in the strips.

For serum samples, three to five times the concentration utilized in the conventional Western Blot assay is required, i.e., a dilution of one part serum to twenty parts buffer as compared to the 1:100 dilution factor used in the Western Blot assay. (See Tsang et al., Method in Enzymology, Vol. 92, 1983.) Theoretically, the actual dilution factor for particular samples may be varied, however, depending upon whether a specimen gives an extremely weak positive response. A PBS-Tween, pH 7.2-7.4 buffer is preferred for the dilution of samples. Preferably, the buffer contains 5% nonfat milk and/or 5% w/v PEG 8000. Typically, 150 ul of a serum sample is mixed with 3 ml of the buffer. But other known buffers may be substituted.

The strips are then incubated with the positive and negative references, controls and test samples at room temperature, preferably for about 10 to 20 minutes, to permit the binding of any antibodies to the viral antigen present in the sample to the antigen in the nitrocellulose strips. A 15 minute incubation period is particularly preferred to insure optimum binding of weak positives. However, if the assay is performed without milk proteins or other binding enhancers such as PEG, a 20 minute incubation period is preferred.

Incubation with the Enzyme-Conjugated Antiserum

The liquid content of each tube is discarded, with the strips remaining in place in the tubes. The strips are then washed, preferably with PBS-Tween buffer at pH 7.2-7.4. In particular, the washing cycle includes four 1 minute washings with PBS-Tween. The strips are then incubated with an enzyme-conjugated anti-human IgM, alone or mixed with an enzyme-conjugated anti-human IgG for about 10 to 20 minutes, at room temperature, to permit binding of the enzyme conjugated antiserum or antisera to any antibody which bound to the antigen during the first incubation period. Goat anti-human antisera-horseradish peroxidase conjugate may be employed, although other enzyme conjugated antisera as are known to those skilled in the art may be used. For example, goat anti-human antisera conjugated with alkaline phosphatase may be used. Again, a 20 minute incubation period is preferred.

As can be appreciated if the assay is to be performed solely to determine whether there is any antibody to the virus present in the sample, irrespective of the antibody class, i.e., IgG or IgM, then both antisera may have the same label, i.e., HRP. Of course, if it is desirable to differentiate between any IgG and IgM antibodies which may be present, it is necessary to employ two different labels. Any labels or combination as are known to those skilled in the art are suitable, for example, goat anti-human IgM labelled with alkaline phosphatase and goat anti-human IgG labelled with horseradish peroxidase are suitable. Horseradish peroxide labelled goat anti-human IgG is available from Protatek International, St. Paul, Minnesota; horseradish peroxidase labelled goat anti-human IgM and alkaline phosphatase labelled goat anti-human IgM are available from Calbiochem as order Nos. 401905 and 401902, respectively.

After completion of the incubation, the liquid content of each tube is discarded. The strips are then washed. Preferably the washing cycle includes four 1 minute washings with PBS-Tween followed by one 1 minute washing with either PBS or distilled water.

Incubation with an Enzyme Substrate

Then, the strips are incubated with one or more enzyme substrates (color change indicators) for about 10 minutes at room temperature, for production of at least one color. Substrate selection is dictated by the enzyme or enzymes used. One appropriate substrate for use with horseradish peroxidase (HRP) enzyme is 3,3'diaminobenzidinetetrahydrochloride dihydrate (DAB). DAB is available from Aldrich Chemical Company, Inc., Milwaukee, Wisc. as Catalog No. 26, 189-0. If as previously described, antisera labelled with different enzymes are used, i.e., horseradish peroxidase and alkaline phosphatase (ALH) are used, then two different substrates should also be used. Thus DAB may be used to develop HRP producing a brown color and BCIP/NBT may be used to develop ALH producing a purple color. BCIP (5-Bromo-4-chloro-3-indolyl phosphate-toluidine salt) is available from Bio-Rad as Catalog No. 170-6539 and NBT (p-Nitro blue tetrazolium chloride) is available from Bio-Rad as Catalog no. 170-6532.

As can be appreciated, this results in a bi-color assay system for detecting and distinguishing IgM and IgG antibodies which reacted with the antigen on the test strip.

In practice, when two different labels are employed the strips are reacted with the substrates sequentially to develop the different colors. For example, in one preferred embodiment the strips are first incubated for 10 minutes with DAB reactive with HRP to produce a brown color. The first color producing reaction is stopped and the liquid is discarded and the strips washed 3 times for 1 minute each with a sodium bicarbonate buffer to deactivate any remaining DAB and adjust the pH of the strips to a pH of approximately 9.2. Then, the strips are incubated for 10 minutes with BCIP/NBT reactive ALH to produce a purple color. BCIP and NBT are prepared and used in accordance with manufacturer's instructions.

It should be understood that the color producing reaction sequence may be reversed so that the ALH is developed first. Moreover, and as previously stated, any known combination of enzymes and substrates may be used. Also, it should be understood that one of the antisera may be fluorescein conjugated rather than enzyme conjugated.

After the final incubation period, the second color producing reaction is stopped by addition of distilled water or 2N $H_2SO_4$ and the results determined according to standard techniques such as those reported by Tsang et al., Methods in Enzymology, Vol. 92 (1983).

In accordance with the present invention, determination of the presence of retroviral antibodies can be accomplished in under 70 minutes. It should be understood that the present assay can also be performed in the absence of milk proteins or PEG. If such assay conditions are selected, it is suggested that maximum incubation times, and maximum antigen-test sample concentrations be used to insure sufficient binding of any antibody present to the antigen.

The Diagnostic Test Kit

In accordance with a preferred embodiment of the invention, a self-contained diagnostic test kit is provided which permits "on site" screening for antibodies to a variety of viruses, including HIV-1, HIV-2, HTLV-I, HTLV-II and Equine Infectious Anemia Virus. The test kit includes a set of tubes containing strong and weak positive and negative references, and at least 1 buffer tube containing a predetermined volume of buffer to which the test sample is added in a predetermined amount to obtain a dilution of from 1:10–1:50, preferably 1:20. A reagent control may also be included.

The reference and control tubes are prediluted, and thus, the user need only dilute the test sample. A set of strip tubes is also provided, each tube containing a nitrocellulose strip containing resolved antigen protein, electrotransferred from an SDS-PAGE gel loaded with from 60-130 ug of protein/10×16 cm gel to obtain a concentration of antigen from 20% to 40% higher than that used in conventional Western Blot.

As indicated hereinabove, in a preferred embodiment a milk protein additive is either pre-dissolved in the buffer solutions containing the test sample and the positive and negative references, or coated on the nitrocellulose strips containing the resolved antigen protein or both. Alternatively, the milk proteins may be separately provided in powder form to be added to the buffer by the user; the resulting buffer solution can then be directly mixed with the test and reference samples, or used to coat the test strips. As previously discussed, PEG may be substituted for milk protein as a binding enhancer or if desired used together with milk protein. Moreover, the assay can be performed in the absence of either milk proteins or PEG.

In a preferred embodiment, the reference, control and sample tubes are numbered. The strip tubes are assigned numbers corresponding to those on the reference control and sample tubes. The strips are assigned numbers corresponding to the tubes in which they are placed. This type of numbering system avoids inadvertent mix-ups which can destroy the accuracy of the assay. As can be appreciated, if the top of a tube containing a positive sample is placed on a tube containing a negative sample, it is likely to obtain a false positive result.

The kit also contains vials of enzyme-conjugated antisera reagents, at least one substrate or color change indicator, washing buffers and at least one solution for terminating the color reaction. Goat anti-human IgG antiserum-horseradish peroxidase and goat anti-human IgM antiserum-alkaline phosphatase are presently preferred as the enzyme conjugated anti-serum reagents. The preferred reaction terminating agent and washing buffers are distilled $H_2O$, and PBS Tween and PBS, respectively.

Preferably, pre-developed positive and negative reference strips and reagent control strips are provided in the kit. These controls are prepared in substantially the same manner as previously described except that after developing, the strips are air dried. The predeveloped strips are used to evaluate the test results by a visual comparison with the test strips after completion of a color reaction. The reagent control, as noted, may be provided to assure the accurate functioning of the reagents. The predeveloped reference and control strips are a significant feature of the present invention because they facilitate reading the assay results and practically eliminate the need for a skilled technician to evaluate the results. Rather than including predeveloped control strips, reading of the assay results may be facilitated by including photographs of strong and weak positive and negative references.

Also, as the kit is self-contained, no laboratory equipment is needed. The advantages of such a kit are apparent, as it facilitates screening for antibodies at any time and virtually at any place, including remote geographic areas and those locations lacking a 24 hour testing facility. As aforementioned, this is of utmost importance in certain organ transplantation situations, in particular, if infection with the AIDS virus is suspected.

The following specific examples of the assay method described herein further illustrate the nature of the present invention, although it is understood that the invention is not limited thereto.

EXAMPLE 1

Detection of IgM Antibody Against HIV-1

70 ug HIV-1 antigen lysate was psoralen/UV inactivated, solubilized with 1.0% TRITON X100 in PBS and electrophoretically resolved in the molecular weight of 12,000–160,000 daltons with a 10% 10×16 cm polyacrylamide gel containing 3% SDS. The resolved antigen was electro-transferred to nitrocellulose paper which was cut into strips. A dilution buffer of PBS-Tween containing 5% by weight Carnation® nonfat milk was prepared. The HIV-1 strips were placed in trays in separate troughs and 3 ml of test samples and controls diluted 1:20 (150 ul into 3 ml buffer), were added to each strip and incubated on a rocker at room temperature for 15 minutes. After completion of the incubation period the liquid from each trough was removed and the strip washed four times for one minute each with a PBS-Tween wash buffer. Then, 3 ml of antihuman IgM conjugated with HRP diluted 1:500 in PBS-Tween was added to each strip and incubated on a rocker for 15 minutes at room temperature. After completion of the incubation, the liquid was removed and the strips washed four times for one minute with 3 ml of PBS-Tween followed by a one-minute washing with 3 ml of PBS alone.

The strips were then incubated with 3 ml of DAB (12.5 mg DAB dissolved in 25 ml of PBS containing 0.01% $H_2O_2$) for 10 minutes at room temperature and covered with aluminum foil to produce color. The color producing reaction was stopped after 10 minutes by adding 3 ml of distilled water to each strip. The results were evaluated by visually comparing the developed test sample strips against the control strips.

EXAMPLE 2

Simultaneous Detection of IgM and IgG Antibody Against HIV-2

HIV-2 viral lysate was inactivated by psoralen/UV treatment and solubilized with 1.0% TRITON X100 in PBS buffer. 85 ug of the inactivated, solubilized lysate were loaded onto a 10×16 cm 10% polyacrylamide gel containing 3% SDS and electrophoretically resolved in the molecular weight range of 12,000–180,000 daltons. The resolved HIV-2 antigen was electro-transferred onto nitrocellulose sheets which was then cut into strips.

The strips, placed into individual troughs on a tray, were incubated on a rocker at room temperature for 15 minutes with 3 ml of known HIV-2 positive test samples (kindly provided by Genetic Systems) diluted 1:20 in PBS-Tween buffer containing 5% by weight of nonfat milk proteins (Carnation® nonfat dry milk) and 5% PEG 8000). The diluent buffer containing both milk protein and PEG is designated CB-Accel buffer. After completion of the incubation period, the liquid was removed and the strips washed 4 times for one minute each with 3 ml of PBS-Tween buffer. The strips were then incubated on a rocker for 15 minutes at room temperature with 3 ml of a mixture of antihuman IgM conjugated with AHL and antihuman IgG conjugated with HRP. Each antiserum was diluted 1:500 in PBS-Tween buffer. After the incubation period, the liquid was removed and the strips were washed with 3 ml of PBS-Tween four times for one minute each followed by a one minute wash with 3 ml of distilled water. Then 3 ml of DAB was (prepared as previously described in Example 1) was added to each strip and incubated for 10 minutes to produce a first color. After completion of the incubation, the liquid was removed and the strips washed twice with 3 ml of sodium bicarbonate buffer at pH 9.2. Then 3 ml of BCIP/NBT in sodium bicarbonate buffer containing 0.01% N.N.dimethylformamide was added to each strip and incubated for 10 minutes at room temperature. The strips were covered with aluminum foil. After completion of the incubation, the second color producing reaction was stopped by adding 3 ml of distilled water. The results were evaluated by visually comparing the developed test sample strips with the control strips.

While preferred embodiments of the invention have been described, it will be apparent to those of ordinary skill in the art that various changes and modifications may be made therein without departing from the spirit and scope of the invention. Accordingly, the above description should be construed as illustrative, and not in a limiting sense, the scope of the invention being defined by the following claims.

We claim:

1. An assay method for detecting IgM antibodies to a retrovirus selected from the group consisting of HIV-1, HIV-2, HTLV-I, and HTLV-II, comprising the steps of, within 70 minutes:
    (a) contacting nitrocellulose paper containing blotted resolved retrovirus antigen protein obtained from gel electrophorectically resolved viral lysate with a test sample and incubating the nitrocellulose paper and test sample to permit binding of antibodies present in the sample to the protein on the nitrocellulose paper wherein
        (1) the viral lysate has an antigen protein concentration at least 20% to 40% greater than the 50–100 ug of antigen protein per 10×16 cm electrophoresis gel utilized in the conventional Western Blot assay; and
        (2) the test sample is diluted in buffer in a ratio of test sample to buffer of from 1:10 to 1:50;
    (b) contacting the incubated nitrocellulose paper of step (a) with an anti-IgM enzyme conjugated antiserum reactive with said antibodies, and incubating to permit binding of the antiserum to said antibodies;
    (c) contacting the incubated nitrocellulose paper of step (b) with an enzyme substrate specific for the enzyme of step (b), and incubating to thereby produce color;
    (d) stopping the color producing reaction of step (c); and
    (e) evaluating the amount of color produced as an indication of the presence of antibodies to the viral lysate.

2. The method of claim 1, wherein the test sample is serum.

3. The method of claim 1, wherein the anti-IgM is conjugated with alkaline phosphatase or horseradish peroxidase.

4. The method of claim 1, wherein step (a) is carried out in the presence of from 3–10% nonfat milk protein.

5. The method of claim 4, wherein the milk protein is mixed with the buffer used to dilute said test sample.

6. The method of claim 4, wherein said milk protein comprises from 60 to 90% by weight casein, and from 10 to 40% by weight of a material selected from the group consisting of lactoglobulin, membrane globulin, alkaline phosphatase, peroxidase catalase, xanthine dehydrogenase, and mixtures thereof.

7. The method of claim 4, wherein the nitrocellulose paper containing the blotted resolved retrovirus antigen protein is coated with milk protein prior to incubation with the test sample in step (a).

8. The method of claim 1, wherein step (a) is carried out in the presence of 3 to 10% polyethylene glycol.

9. The method of claim 8, wherein the polyethylene glycol is mixed with the buffer used to dilute said test sample.

10. The method of claim 7, wherein the viral lysate has an antigen protein concentration of between 60–130 ug per $10 \times 16$ cm gel.

11. The method of claim 7, in which step (a) is repeated with at least one positive control (a sample containing antibodies to said retrovirus) and one negative control (a sample that is devoid of antibodies to said retrovirus) in place of the test sample, the reaction product formed thereby is subjected to steps (b–e), and the colors produced as compared as standards with the color produced from the test sample, to evaluate the presence of antibodies to the retrovirus in the test sample.

12. An assay method for simultaneously detecting IgG and IgM antibodies to a retrovirus selected from the group consisting of HIV-1, HIV-2, HTLV-I, and HTLV-II, comprising the steps of, within 70 minutes:
 (a) contacting nitrocellulose paper containing blotted resolved retrovirus antigen protein obtained from gel electrophorectically resolved viral lysate with a test sample and incubating the nitrocellulose paper and test sample to permit binding of antibodies present in the sample to the protein on the nitrocellulose paper wherein
  (1) the viral lysate has an antigen protein concentration at least 20% to 40% greater than the 50–100 ug of antigen protein per $10 \times 16$ cm electrophoresis gel utilized in the conventional Western Blot assay; and
  (2) the test sample is diluted in buffer in a ratio of test sample to buffer of from 1:10 to 1:50;
 (b) contacting the incubated nitrocellulose paper of step (a) with an anti-IgM enzyme conjugated antiserum reactive with said antibodies and with an anti-IgG enzyme conjugated antiserum reactive with said antibodies, and incubating to permit binding of said antisera to said antibodies;
 (c) contacting the incubated nitrocellulose paper of step (b) with at least one enzyme substrate specific for the enzyme or enzymes of step (b), and incubating to thereby produce color;
 (d) stopping the color producing reaction of step (c); and
 (e) evaluating the amount of color produced as an indication of the presence of IgM and IgG antibodies to the viral lysate.

13. The method of claim 12, wherein the test sample is serum.

14. The method of claim 12, wherein the anti-IgM antiserum is conjugated with one enzyme and the anti-IgG antiserum is conjugated with a different enzyme.

15. The method of claim 14, wherein the enzymes are horseradish peroxidase and alkaline phosphatase.

16. The method of claim 12, wherein step (a) is carried out in the presence of from 3–10% nonfat milk protein.

17. The method of claim 16, wherein the milk protein is mixed with the buffer used to dilute said test sample.

18. The method of claim 16, wherein said milk protein comprises from 60 to 90% by weight casein, and from 10 to 40% by weight of a material selected from the group consisting of lactoglobulin, membrane globulin, alkaline phosphatase, peroxidase catalase, xanthine dehydrogenase, and mixtures thereof.

19. The method of claim 16, wherein the nitrocellulose paper containing the blotted resolved retrovirus antigen protein is coated with milk protein prior to incubation with the test sample in step (a).

20. The method of claim 12, wherein step (a) is carried out in the presence of from 3 to 10% polyethylene glycol.

21. The method of claim 20, wherein the polyethylene glycol is mixed with the buffer used to dilute said test sample.

22. The method of claim 12, wherein the viral lysate has an antigen protein concentration of between 60–130 ug per $10 \times 16$ cm gel.

23. The method of claim 12, in which step (a) is repeated with at least one positive control (a sample containing antibodies to said retrovirus) and one negative control (a sample that is devoid of antibodies to said retrovirus) in place of the test sample, the reaction product formed thereby is subjected to steps (b–e), and the colors produced are compared as standards with the color produced from the test sample, to evaluate the presence of antibodies to the retrovirus in the test sample.

24. A diagnostic test kit for simultaneously detecting, within 70 minutes, IgG and IgM antibodies which bind to an antigen of a retrovirus selected from the group consisting of HIV-1, HIV-2, HTLV-I, and HTLV-II, comprising:
 (a) a set of control tubes comprising positive and negative references;
 (b) at least one reagent control tube;
 (c) at least one dilution tube containing a predetermined volume of buffer for dilution of test samples in a ratio of test sample to buffer of from 1:10 to 1:50;
 (d) a set of tubes containing nitrocellulose test strips containing resolved retroviral antigen, said antigen being obtained from gel electrophorectically resolved viral lysate, wherein the resolved retroviral antigen is present in a concentration at least 20% to 40% greater than the 50–100 ug of antigen protein per $10 \times 16$ cm electrophoresis gel utilized in the conventional Western Blot assay;
 (e) an anti-IgG enzyme conjugated antiserum and an anti-IgM enzyme conjugated antiserum for reacting with said antibodies;
 (f) at least one color producing enzyme substrate specific for the enzyme or enzymes of step (e) wherein the color produced is an indicator to ascertain whether the antibodies are present; and
 (g) predeveloped positive and negative reference strips and reagent control strips for evaluating the results of the test by visually comparing the predeveloped strips with the test strips after completion of a color change reaction.

25. The diagnostic test kit of claim 24, wherein the dilution tubes contain 3-10% nonfat milk protein dissolved in the buffer.

26. The diagnostic test kit of claim 25, wherein said milk protein comprises from 60 to 90% by weight casein, and from 10 to 40% by weight of a material selected from the group consisting of lactoglobulin, membrane globulin, alkaline phosphatase, peroxidase catalase, xanthine dehydrogenase, and mixtures thereof.

27. The diagnostic test kit of claim 24, further comprising a nonfat milk protein reagent for binding with the resolved retroviral antigen, said reagent being dissolved in the buffer in dilution tube (c) or coated on the nitro-cellulose test strips in tubes (d).

28. The diagnostic test kit of claim 24, wherein the dilution tubes contain from about 3 to 10% polyethylene glycol.

29. The diagnostic test kit of claim 28, wherein the polyethylene glycol is mixed with the buffer of step (c).

30. The diagnostic test kit of claim 24, wherein the anti-IgM antiserum is conjugated with one enzyme and the anti-IgG antiserum is conjugated with a different enzyme.

31. The diagnostic test kit of claim 30, wherein the IgM antiserum is conjugated with alkaline phosphatase and the IgG antiserum is conjugated with horseradish peroxidase.

32. The diagnostic test kit of claim 24, wherein the electrophoretically resolved antigen has a concentration of 60 to 130 ug per 10×16 cm gel.

33. A diagnostic test kit for simultaneously detecting, within 70 minutes, IgM antibodies which bind to an antigen of a retrovirus selected from the group consisting of HIV-1, HIV-2, HTLV-I, and HTLV-II, comprising:
  (a) a set of control tubes comprising positive and negative references;
  (b) at least one reagent control tube;
  (c) at least one dilution tube containing a predetermined volume of buffer for dilution of test samples in a ratio of test sample to buffer of from 1:10 to 1:50;
  (d) a set of tubes containing nitrocellulose test strips containing resolved retroviral antigen, said antigen being obtained from gel electrophoretically resolved viral lysate, wherein the resolved retroviral antigen is present in a concentration at least 20% to 40% greater than the 50-100 ug of antigen protein per 10×16 cm electrophoresis gel utilized in the conventional Western Blot assay;
  (e) an anti-IgM enzyme conjugated antiserum for reacting with said antibodies;
  (f) at least one color producing enzyme substrate specific for the enzyme of step (e) wherein the color produced is an indicator to ascertain whether the antibodies are present; and
  (g) predeveloped positive and negative reference strips and reagent control strips for evaluating the results of the test by visually comparing the predeveloped strips with the test strips after completion of a color change reaction.

34. The diagnostic test kit of claim 33, wherein the dilution tubes contain 3-10% nonfat milk protein dissolved in the buffer.

35. The diagnostic test kit of claim 33, further comprising a nonfat milk protein reagent for binding with the resolved retroviral antigen, said reagent being dissolved in the buffer in dilution tube (c) or coated on the nitro-cellulose test strips in tubes (d).

36. The diagnostic test kit of claim 33, wherein the dilution tubes contain from about 3 to 10% polyethylene glycol.

37. The diagnostic test kit of claim 36, wherein the polyethylene glycol is mixed with the buffer of step (c).

38. The diagnostic test kit of claim 33, wherein the electrophoretically resolved antigen has a concentration of 60 to 130 ug per 10×16 cm gel.

39. The diagnostic test kit of claim 33, wherein said milk protein comprises from 60 to 90% by weight casein, and from 10 to 40% by weight of a material selected from the group consisting of lactoglobulin, membrane globulin, alkaline phosphatase, peroxidase catalase, xanthine dehydrogenase, and mixtures thereof.

* * * * *

UNITED STATES PATENT AND TRADEMARK OFFICE
CERTIFICATE OF CORRECTION

PATENT NO. : 5,093,230

DATED : March 3, 1992

INVENTOR(S): Kurt B. Osther, Louis M. Dyll

It is certified that error appears in the above-identified patent and that said Letters Patent is hereby corrected as shown below:

Col. 3, line 60: Change "in Methods of Enzymology," to --In: Methods in Enzymology,--.

Col. 6, line 3: Change "Method" to --Methods--.

Claim 1, col. 10, line 33: Change "electrophorectically" to --electrophoretically--.

Claim 10, col. 11, line 16: Change "claim 7" to --claim 1--.

Claim 11, col. 11, line 19: Change "claim 7" to --claim 1--.

Claim 11,, col. 11, line 25: Change "as compared" to --are compared--.

Claim 12, col. 11, line 35: Change "electrophorectically" to --electrophoretically--.

Claim 24, col. 12, line 12: Change "electrophorectically" to --electrophoretically--.

Claim 31, col. 13, line 25: Change "IgM" to --anti-IgM--.

UNITED STATES PATENT AND TRADEMARK OFFICE
CERTIFICATE OF CORRECTION

PATENT NO. : 5,093,230
DATED : March 3, 1992
INVENTOR(S) : Kurt B. Osther, et al.

It is certified that error appears in the above-indentified patent and that said Letters Patent is hereby corrected as shown below:

Column 13, claim 13, line 26, change "IgG" to --anti-IgG--.

Signed and Sealed this

Twenty-second Day of February, 1994

Attest:

BRUCE LEHMAN

*Attesting Officer*     *Commissioner of Patents and Trademarks*